US011198921B2

(12) United States Patent
Rogers et al.

(10) Patent No.: US 11,198,921 B2
(45) Date of Patent: Dec. 14, 2021

(54) IONIC LIQUID SOLVENTS OF PERHALIDE TYPE FOR METALS AND METAL COMPOUNDS

(71) Applicant: Petroliam Nasional Berhad (Petronas), Kuala Lumpur (MY)

(72) Inventors: Robin Don Rogers, Antrim (GB); John Holbrey, Antrim (GB)

(73) Assignee: Petroliam Nasional Berhad (Petronas), Kuala Lumpur (MY)

( * ) Notice: Subject to any disclaimer, the term of this patent is extended or adjusted under 35 U.S.C. 154(b) by 262 days.

(21) Appl. No.: 16/372,614

(22) Filed: Apr. 2, 2019

(65) Prior Publication Data
US 2019/0360069 A1    Nov. 28, 2019

Related U.S. Application Data

(63) Continuation of application No. 13/263,097, filed as application No. PCT/GB2010/050551 on Mar. 30, 2010, now Pat. No. 10,266,913.

(30) Foreign Application Priority Data

Apr. 6, 2009 (GB) .................................... 0905894

(51) Int. Cl.
*C22B 3/04*   (2006.01)
*C07C 211/63* (2006.01)
*C07D 233/58* (2006.01)
*C22B 3/10*   (2006.01)
*C22B 11/00*  (2006.01)
*C22B 11/06*  (2006.01)
*C22B 43/00*  (2006.01)

(52) U.S. Cl.
CPC .............. *C22B 3/04* (2013.01); *C07C 211/63* (2013.01); *C07D 233/58* (2013.01); *C22B 3/10* (2013.01); *C22B 11/04* (2013.01); *C22B 11/06* (2013.01); *C22B 43/00* (2013.01); *Y02P 10/20* (2015.11); *Y02P 20/54* (2015.11)

(58) Field of Classification Search
CPC .. C22B 3/04; C22B 3/10; C22B 11/04; C22B 11/06; C22B 43/00; C07C 211/63
USPC ........................................................ 75/300
See application file for complete search history.

(56) References Cited

U.S. PATENT DOCUMENTS

| 4,684,404 A | 8/1987  | Kalocsai     |
| 5,120,523 A | 6/1992  | Nakao et al. |
| 5,264,191 A | 11/1993 | Nakao et al. |
| 5,607,619 A | 3/1997  | Dadgar et al.|
| 5,620,585 A | 4/1997  | Dadgar et al.|
| 6,379,634 B1| 4/2002  | Fields et al.|
| 6,475,451 B1| 11/2002 | Leppin et al.|
| 7,901,486 B2| 3/2011  | Cross et al. |
| 8,361,300 B2| 1/2013  | Kuzmanovic et al. |
| 2002/0198100 A1 | 12/2002 | Mehnert et al. |
| 2011/0085952 A1 | 4/2011  | Sasson et al. |
| 2014/0001100 A1 | 1/2014  | Abai et al. |

FOREIGN PATENT DOCUMENTS

| EP | 1780803 A1 | 5/2007 |
| JP | 11257258 | 10/1989 |
| JP | H04107223 A | 4/1992 |
| WO | 8912604 A1 | 12/1989 |
| WO | 9806106 A2 | 2/1998 |
| WO | 0056700 A1 | 9/2000 |
| WO | 0226701 A2 | 4/2002 |
| WO | WO-03086605 A2 * | 10/2003 | ......... B01D 53/1456 |

OTHER PUBLICATIONS

Abbott, A. P, et al., "Electropolishing of stainless steels in a choline chloride based ionic liquid: an electrochemical study with surface characterisation using SEM and atomic force microscopy," Phys. Chem. Chem. Phys., 2006, vol. 8, pp. 4214-4221.
Abbott, A. P, "Solubility of Metal Oxides in Deep Eutectic Solvents Based on Choline Chloride," J. Chem. Eng. Data, 2006, pp. 1280-1282.
Abbott a.P et al.,"Electropolishing of stainless steel in an ionic liquid," Trans. Inst. Metal Finishing, 2005, vol. 83, pp. 51-53.
Abbott, et al., "Selective Extraction of Metals from Mixed Oxide Matrixes Using Choline-Based Ionic Liquids," Inorg. Chem., 2005, vol. 44, pp. 6497-6499.
Aldous L. et al.,"Electrochemical studies of gold and chloride in ionic liquids," New J. Chem., 2006, vol. 30, pp. 1576-1583.
Bagno A. et al.,"The effect of the anion on the physical properties of trihalide-based N,N-dialkylimidazolium ionic liquids," Org. Biomol. Chem., 2005, vol. 3, pp. 1624-1630.
Bao W. et al., "An effective synthesis of bromoesters from aromatic aldehydes using tribromide ionic liquid based on L-prolinol as reagent and reaction medium under mild conditions," Green Chem., 2006, vol. 8, pp. 1028-1033.
Bao W. et al., "Synthesis of vinyl bromides from the reaction of alpha., carboxylic acids with ionic liquid [bmim][Br. sub.3]/[bmim]Br" J. Chem. Res., 2005, pp. 617-619.
Billard I. et al., "Dissolution of UO.sub.2, UO.sub.3 and of some lanthanide oxides in BumimTf.sub.2N: effect of acide and water and formation of UO.sub.2(Numbersub.3).sub.3," Dalton Trans., 2007, 4214-4221.
Chen P. Y., et al., "The electrodeposition of Mn and Zn—Mn allows from the room-temperature tri-1-butylmethylammonium bis ((trifluoromethane) sulfonyl) imide ionic liquid," Electrochimica Acta, 2007, vol. 52, pp. 1857-1864.

(Continued)

*Primary Examiner* — Melissa S Swain
(74) *Attorney, Agent, or Firm* — Ryan T. Grace; Advent, LLP

(57) ABSTRACT

The present invention relates to a process for dissolving metals in perhalide containing ionic liquids, and to the extraction of metals from mineral ores; the remediation of materials contaminated with heavy, toxic or radioactive metals; and to the removal of heavy and toxic metals from hydrocarbon streams.

24 Claims, No Drawings

(56) References Cited

OTHER PUBLICATIONS

Chiappe C. et al., "Highly efficient bromination of aromatic compounds using 3-methylimidazolium tribromide as reagent/solvent," Chem. Commun., 2004, 2536-2537).

Chiappe C. et al., "Bromination of Alkynes in Ionic Liquids=A Kinetic Investigation," Eur. J. Org. Chem., 2002, 2831-2837.

Database WPI Week 200280, Thomson Scientific, London, GB; 2002-733977, XP002585218 & CN 1363723, Aug. 14, 2002, abstract.

Gorlov, M., et al., "Ionic liquid electrolytes for dye-sensitized solar cells," Dalton Trans., 2008, 2655-2666.

Hussey C. L., et al., "Electrodissolution and Electrodeposition of Lead in an Acidic Room Temperature Chloroaluminate Molten Salt," J. Electrochem. Soc., 1991, 138, 1886-1890.

International Preliminary Report on Patentability dated Oct. 11, 2011, in Application No. PCT/GB2010/050551.

International Search Report dated Jun. 10, 2010, in Application No. PCT/GB2010/050551.

Ji et al., "Pyrrolidinium Imides: Promising Ionic Liquids for Direct Capture of Elemental Mercury from Flue Gas," Water, Air, & Soil Pollution: Focus, 2008, vol. 8, pp. 349-358.

Ji et al., "Room Temperature Ionic Liquids for Mercury Capture from Flue Gas," Ind. Eng. Chem. Res., 2008, vol. 47, pp. 8396-8400.

Liu et al., "Using Bromine Gas To Enhance Mercury Removal from Flue Gas of Coal-Fired Power Plants," Environ. Sci. Technol., 2007, vol. 41, pp. 1405-1412.

Nockemann P. et al., "Task-Specific Ionic Liquid for Solubilizing Metal Oxides," J. Phys. Chem. B, 2006, 110, 20978-20992.

S. E. Lindberg et al., "Dynamic Oxidation of Gaseous Mercury n the Arctic Troposhere at Polar Sunrise," Environ. Sci. Technol., 2002, 36, 1245-1256.

Salazar J. et al., "Pentylpyridnium Tribromide: A Vapor Pressure Free Room Temperature Ionic Liquid Analogue of Bromine," Synlett, 2004, 1318-1320.

Seddon K. R. et al., "Neoteric optical media for refractive index determination of gems and minerals," New J. Chem., 2006, 30, 317-326.

Whitehead J. A. et al., "Green' leaching: recyclable and selective leaching of gold-bearing ore in an ionic liquid," Green Chem., 2004, 6, 313-315.

Z. Wang et al., "Oxidation of elemental mercury by aqueous bromine: atmospheric implications," Atmospheric Environment, 2004, 38, 3675-3688.

Zevenhoven, (Flue Gases and Fuel gases, Jun. 2001).

\* cited by examiner

IONIC LIQUID SOLVENTS OF PERHALIDE TYPE FOR METALS AND METAL COMPOUNDS

The present invention relates to a process for dissolving metals in ionic liquids. More specifically, the invention relates to a process for dissolving metals in ionic liquids that comprise perhalide anions. The process of the invention may be applied to the extraction of metals from mineral ores; to the remediation of materials contaminated with heavy, toxic or radioactive metals; and to the removal of heavy and toxic metals from hydrocarbon streams. The invention further relates to novel compositions comprising metals dissolved in ionic liquids.

The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations, such as imidazolium and pyridinium-based cations. In room temperature ionic liquids, the structures of the cation and anion prevent the formation of an ordered crystalline structure and therefore the salt is liquid at room temperature.

Ionic liquids are most widely known as solvents due to favourable properties including negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

In WO 98/06106, a process is disclosed for the oxidative dissolution of nuclear fuels and nuclear fuel-cladding materials in nitrate-based ionic liquids. The ionic liquids disclosed comprise nitrate anions, and optionally sulphate or tetrafluoroborate anions, and a Bronsted or Franklin acid (such as nitric acid, sulphuric acid, or nitronium cations) which is necessary to increase the oxidising power of the solvent. The ionic liquids disclosed are all water soluble.

Pitner, W. R. et al. have described a similar process for dissolving insoluble uranium oxide ($UO_2$) in which the uranium oxide is oxidised to the soluble species $UO_2^{2+}$ in a mixture of nitric acid and an ionic liquid comprising nitrate anions (*Mathematics, Physics and Chemistry*, 2003, 92, 209-226). The dissolution of elemental metals is not described, however.

Whitehead, J. A., et al. have described the use of ionic liquids having hydrogensulfate anions, containing iron(III) sulfate as an oxidant and thiourea as a complexant, as leaching solutions to extract gold and silver from mineral ores (*Green Chem.*, 2004, 6, 313-315). The ionic liquid is used as a non-volatile, water-miscible solvent in which the oxidising and complexing components are present as additives.

Metal oxide dissolution in choline chloride-based deep eutectic solvents has been reported by Abbot, A. P., et al. (*J. Chem. Eng. Data*, 2006, 51, 1280-1282; and *Inorg. Chem.*, 2005, 44, 6497-6499).

Billard, I., et al. have described the dissolution of uranium oxides and lanthanide oxides in 1-butyl-3-methylimidazolium bistriflimide upon the addition of a nitrate source as an oxidant (*Dalton Trans.*, 2007, 4214-4221), and Nockemann, P., et al. have described the dissolution of metal oxides in a betaine bistriflimide ionic liquid in the presence of water (*J. Phys. Chem. B*, 2006, 110, 20978-20992).

Ji, L. et al. have described an approach to the capture of elemental mercury from coal combustion flue gases by oxidation of the mercury by permanganate dissolved in an ionic liquid coated onto a silica support (*Water, Air & Soil Pollution: Focus*, 2008, 8, 349-358).

In addition, the direct electrochemical anodic dissolution of metals into ionic liquids has been described by Abbot, A. P., et al. (*Phys. Chem. Chem. Phys.*, 2006, 8, 4214-4221; and *Trans. Inst. Metal Finishing*, 2005, 83, 51-53); Chen, P.-Y., et al. (*Electrochimica Acta*, 2007, 52, 1857-1864); Hussey, C. L., et al. (*J. Electrochem. Soc.*, 1991, 138, 1886-1890); and by Aldous, L. et al. (*New J. Chem.*, 2006, 30, 1576-1583).

Notably, none of these reports discloses the direct dissolution of elemental metals, alloys, or metal compounds in ionic liquids in the absence of added solvents and/or oxidising agents.

Elemental mercury forms amalgams with gold, zinc and many metals and reacts with oxygen in air when heated to form mercury oxide, which then can be decomposed by further heating to higher temperatures. Mercury does not react with most acids, such as dilute sulfuric acid, though oxidising acids such as concentrated sulfuric acid and nitric acid or aqua regia dissolve it to give sulfate and nitrate and chloride. Mercury reacts with atmospheric hydrogen sulfide and even with solid sulfur flakes. This reaction of mercury with elemental sulfur is utilised used in mercury spill kits which contain sulfur powder to absorb mercury vapours (spill kits also use activated charcoal and powdered zinc to absorb and amalgamate mercury).

The reactivity of elemental mercury to bromine and chlorine is well known, as a basic chemical reaction (for example, see Cotton and Wilkinson, *Comprehensive Inorganic Chemistry*, 4th Edition, p 592), and has been recognised as one mechanism for the formation of inorganic mercury species in the atmosphere (see for example, Z. Wang et al., *Atmospheric Environment*, 2004, 38, 3675-3688 and S. E. Lindberg, et al., *Environ. Sci. Technol.*, 2002, 36, 1245-1256). This reactivity of mercury with halogens has been utilised in flue-gas scrubbing technologies to remove mercury vapour by high temperature reaction with either bromine or chlorine forming inorganic mercury species that are readily extracted into aqueous media (for example, S-H. Lui, et al., *Environ. Sci. Technol.*, 2007, 41, 1405-1412).

Bromine has been used for leaching of gold from ores (used either directly, or produced in situ from bromide salts and chlorine gas), however this approach has been superseded by economically cheaper cyanide leaching processes.

When working with bromine or chlorine under ambient or near-ambient temperatures and pressures, there are significant difficulties and hazards that are associated with the corrosivity and toxicity of both bromine and chlorine vapours as well as the incompatibility of the halogens with many metals. Bromine is known to oxidise many metals to their corresponding bromide salts, with anhydrous bromine being less reactive toward many metals than hydrated bromine. Dry bromine reacts vigorously with aluminium, titanium, mercury as well as alkaline earths and alkali metals forming metal bromide salts.

Organic perhalide salts (also known as trihalide salts) have a variety of known applications, including use as sterilising agents; for bleaching of textiles; for wart removal; and as aqueous antifouling agents. In addition, organic perhalide salts may be used as highly efficient brominating agents in the preparation of brominated organic compounds, including those having anti-inflammatory, antiviral, antibacterial, antifungal, and flame-retardant properties.

The use of aqueous inorganic perbromide salt solutions as leaching agents for gold, silver, platinum and palladium has been described in U.S. Pat. No. 5,620,585.

Many ionic liquids incorporating perhalide anions have been reported (see Bagno, A., et al., *Org. Biomol. Chem.*, 2005, 3, 1624-1630, for example). Applications of these ionic liquids include use as brominating media for organic compounds (Bao, W., et al. *Green Chem.*, 2006, 8, 1028-1033; Bao, W., et al., *J. Chem. Res.*, 2005, 617-619; Chiappe, C., et al., *Chem. Commun.*, 2004, 2536-2537; Salazar, J. et al., *Synlett*, 2004, 1318-1320; Chiappe, C., et al., *Eur. J. Org. Chem.*, 2002, 2831-2837), as high refractive index fluids (Seddon, K. R., et al., *New J. Chem.*, 2006, 30, 317-326), and as components in photovoltaic cells (Gorlov, M., et al., *Dalton Trans.*, 2008, 2655-2666).

In addition, ionic liquids comprising perhalide anions have lower viscosities than the corresponding halide ionic liquids, and are hydrophobic, forming stable biphases with water.

The present invention is based on the discovery that ionic liquids comprising perhalide anions can dissolve metals and metal compounds without the need for additional solvents and/or oxidising agents.

In a first aspect, the present invention provides method for dissolving a metal comprising contacting the metal with an ionic liquid having the formula:

[Cat$^+$][X$^-$]

wherein: [Cat$^+$] represents one or more cationic species, and

[X$^-$] represents one or more perhalide anions, wherein the ionic liquid is free of additional solvents and/or oxidants.

The use of ionic liquids comprising perhalide anions provides a number of advantages over the ionic liquids that have previously been used for the dissolution of metals and metal compounds. In particular, ionic liquids comprising perhalide anions are stable to air and moisture, in contrast with the air- and moisture-unstable haloaluminate ionic liquids that have been used for electrodissolution of metals.

In addition, ionic liquids comprising perhalide anions are generally hydrophobic, and therefore suitable for extracting metals and metal compounds from aqueous solutions. This is in contrast to hydrogensulfate-based systems for leaching gold and silver ores, nitrate-based systems for nuclear fuel processing, and choline chloride-based deep eutectic fluids described above, in which the ionic liquids used are water-miscible. Thus, the present invention provides a non-aqueous and water-immiscible solvent system for the dissolution of metals and metal-containing compounds.

According to the method of the present invention, [X$^-$] preferably comprises one or more perhalide anions selected from [I$_3$]$^-$, [BrI$_2$]$^-$, [Br$_2$I]$^-$, [ClI$_2$]$^-$, [Br$_3$]$^-$, [ClBr$_2$], [BrCl$_2$]$^-$, [ICl$_2$]$^-$, or [Cl$_3$]; more preferably [X$^-$] comprises one or more perhalide anions selected from [BrI$_2$]$^-$, [Br$_2$I]$^-$, [ClI$_2$]$^-$, [ClBr$_2$]$^-$, or [BrCl$_2$]$^-$; still more preferably [X$^-$] comprises one or more perhalide anions selected from [Br$_2$I]$^-$, [ClBr$_2$]$^-$, or [BrCl$_2$]$^-$; and most preferably [X$^-$] is [ClBr$_2$]$^-$. In a further embodiment, [X$^-$] comprises one or more perhalide anions selected from [I$_3$]$^-$, [Br$_3$]$^-$, or [Cl$_3$]$^-$, and is more preferably [Br$_3$]$^-$.

In accordance with the present invention, [Cat$^+$] may be a cationic species selected from: ammonium, azaannulenium, azathiazolium, benzimidazolium, benzofuranium, benzotriazolium, borolium, cinnolinium, diazabicyclodecenium, diazabicyclononenium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxathiazolium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, sulfonium, tetrazolium, iso-thiadiazolium, thiazinium, thiazolium, thiophenium, thiuronium, triazadecenium, triazinium, triazolium, iso-triazolium, and uronium.

In another embodiment, [Cat$^+$] is a quaternary nitrogen-containing heterocyclic cation selected from:

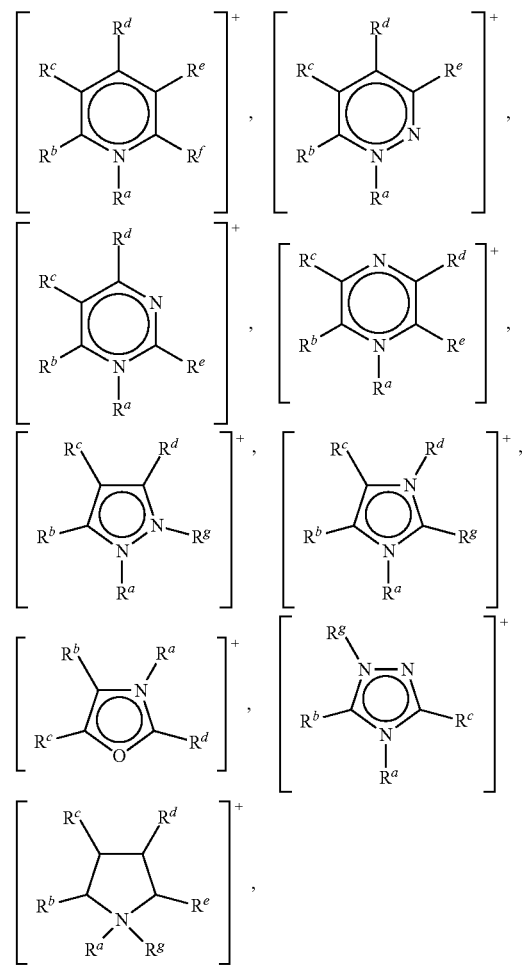

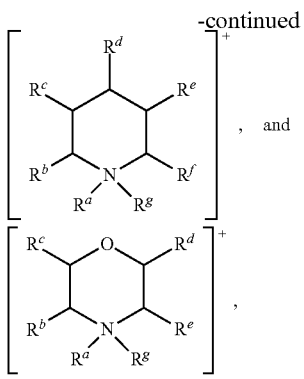
, and wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —$(CH_2)_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —$NO_2$, —$CO_2R^x$, —$OC(O)R^x$, —$C(O)R^x$, —$C(S)R^x$, —$CS_2R^x$, —$SC(S)R^x$, —$S(O)(C_1$ to $C_6)$alkyl, —$S(O)O(C_1$ to $C_6)$alkyl, —$OS(O)(C_1$ to $C_6)$alkyl, —$S(C_1$ to $C_6)$alkyl, —S—$S(C_1$ to $C_6$ alkyl), —$NR^xC(O)NR^yR^z$, —$NR^xC(O)OR^y$, —$OC(O)NR^yR^z$, —$NR^xC(S)OR^y$, —$OC(S)NR^yR^z$, —$NR^xC(S)SR^y$, —$SC(S)NR^yR^z$, —NR C$(S)NR^yR^z$, —$C(O)NR^yR^z$, —$C(S)NR^yR^z$, —$NR^yR^z$, or a heterocyclic group, wherein $R^x$, $R^y$ and $R^z$ are independently selected from hydrogen or $C_1$ to $C_6$ alkyl.

More preferably, $R^a$, $R^b$, $R^c$, $R^d$, $R^e$, $R^f$ and $R^g$ are each independently selected from hydrogen, $C_1$ to $C_{20}$ straight chain or branched alkyl group, a $C_3$ to $C_6$ cycloalkyl group, or a $C_6$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —$NO_2$, —$CO_2(C_1$ to $C_6)$alkyl, —$OC(O)(C_1$ to $C_6)$alkyl, $C_6$ to $C_{10}$ aryl and $C_7$ to $C_{10}$ alkaryl.

$R^a$ is preferably selected from $C_1$ to $C_{30}$, linear or branched, alkyl, more preferably $C_2$ to $C_{20}$ linear or branched alkyl, still more preferably, $C_1$ to $C_{10}$ linear or branched alkyl, and most preferably $C_1$ to $C_5$ linear or branched alkyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_1$ to $C_{10}$ linear or branched alkyl, still more preferably, $C_1$ to $C_5$ linear or branched alkyl, and most preferably $C_2$ to $C_5$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_5$ alkoxyalkyl.

In further preferred embodiments, $R^b$, $R^c$, $R^d$, $R^e$, and $R^f$ are independently selected from hydrogen and $C_1$ to $C_5$ linear or branched alkyl, and more preferably $R^b$, $R^c$, $R^d$, $R^e$, and $R^f$ are hydrogen.

In a preferred embodiment of the invention, [Cat$^+$] is selected from:

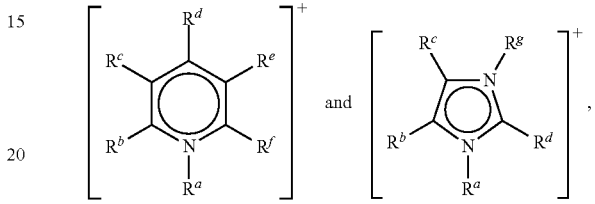

wherein: $R^a$, $R^b$, $R^c$, $R^d$, $R^e$, $R^f$, and $R^g$ are as defined above.

More preferably, [Cat$^+$] is selected from:

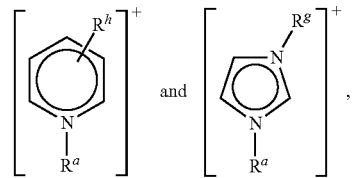

wherein: $R^a$ and $R^g$ are as defined above, and $R^h$ represents hydrogen or a methyl group.

Specific examples of preferred cations include:

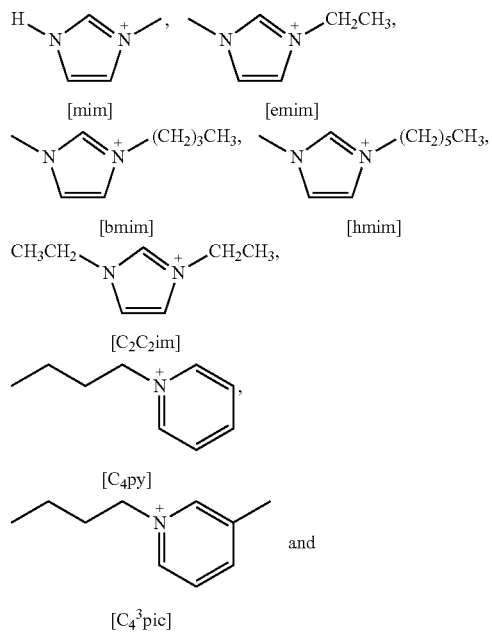

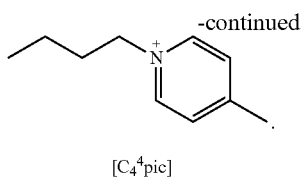

[C₄⁴pic]

In another preferred embodiment of the invention, [Cat⁺] is selected from:

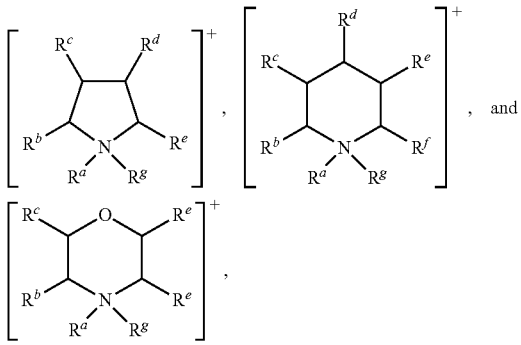

wherein: $R^a$, $R^b$, $R^c$, $R^d$, $R^e$, $R^f$, and $R^g$ are as defined above.

Still more preferably, [Cat⁺] is selected from:

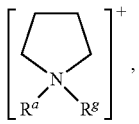

wherein: $R^a$, $R^b$, $R^c$, $R^d$, $R^e$, $R^f$, and $R^g$ are as defined above.

Specific examples of preferred cations include:

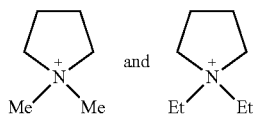

In another preferred embodiment of the invention, [Cat⁺] is an acyclic cation selected from:

[N($R^a$)($R^b$)($R^c$)($R^d$)]⁺, [P($R^a$)($R^b$)($R^c$)($R^d$)]⁺, and [S($R^a$)($R^b$)($R^c$)]⁺, wherein: $R^a$, $R^b$, $R^c$, and $R^d$ are each independently selected from a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —(CH$_2$)$_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO$_2$, —CO$_2$R$^x$, —OC(O)R$^x$, —C(O)R$^x$, —C(S)R$^x$, —CS$_2$R$^x$, —SC(S)R$^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^1$C(S)NR$^y$R$^z$, —C(O)NR$^y$R$^z$, —C(S)NR$^y$R$^z$, —NR$^y$R$^z$, or a heterocyclic group, wherein R$^x$, R$^y$ and R$^z$ are independently selected from hydrogen or $C_1$ to $C_6$ alkyl, and wherein one of $R^a$, $R^b$, $R^c$, and $R^d$ may also be hydrogen.

More preferably, [Cat⁺] is selected from:

[N($R^a$)($R^b$)($R^c$)($R^d$)]⁺ and [P($R^a$)($R^b$)($R^c$)($R^d$)]⁺, wherein: $R^a$, $R^b$, $R^c$, and $R^d$ are each independently selected from a $C_1$ to $C_{15}$ straight chain or branched alkyl group, a $C_3$ to $C_6$ cycloalkyl group, or a $C_6$ aryl group, wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, —CN, —OH, —SH, —NO$_2$, —CO$_2$($C_1$ to $C_6$)alkyl, —OC(O)($C_1$ to $C_6$)alkyl, $C_6$ to $C_{10}$ aryl and $C_7$ to $C_{10}$ alkaryl, and wherein one of $R^a$, $R^b$, $R^c$, and $R^d$ may also be hydrogen.

Further examples include wherein $R^a$, $R^b$, $R^c$ and $R^d$ are independently selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl. More preferably two or more, and most preferably three or more, of $R^a$, $R^b$, $R^c$ and $R^d$ are independently selected from methyl, ethyl, propyl and butyl.

In a further preferred embodiment, $R^b$, $R^c$, and $R^d$ are each the same alkyl group selected from methyl, ethyl n-butyl, and n-octyl, and $R^a$ is selected from hydrogen, methyl, n-butyl, n-octyl, n-tetradecyl, 2-hydroxyethyl, or 4-hydroxy-n-butyl.

Specific examples of preferred ammonium and phosphonium cations suitable for use according to the present invention include:

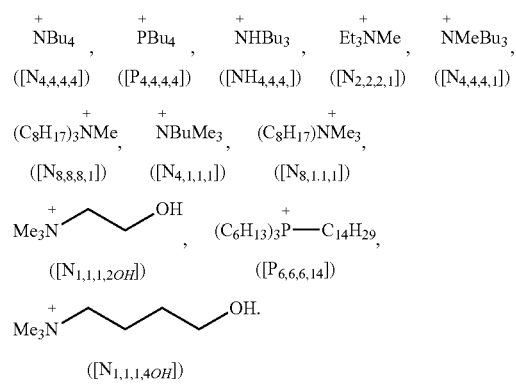

In a preferred embodiment, [Cat⁺] is selected from:

[N($R^a$)($R^b$)($R^c$)($R^d$)]⁺ and [P($R^a$)($R^b$)($R^c$)($R^d$)]⁺, wherein: $R^a$, $R^b$, $R^c$, and $R^d$ are each independently selected from a $C_1$ to $C_5$ straight chain or branched alkyl group.

In the preferred embodiment where $R^a$, $R^b$, $R^c$, and $R^d$ are each independently selected from a $C_1$ to $C_5$ straight chain or branched alkyl group, the preferred compounds may be selected from:

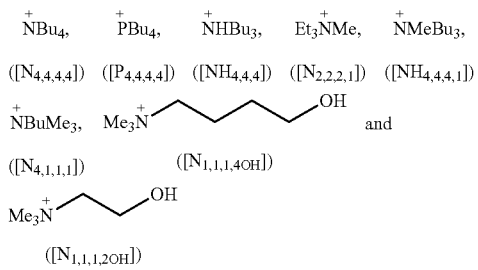

The present invention is not limited to ionic liquids comprising cations having only a single charge. Thus, the formula [Cat⁺][X⁻] is intended to encompass ionic liquids comprising, for example, doubly, triply and quadruply charged cations. The relative stoichiometric amounts of [Cat⁺] and [X⁻] in the ionic liquid are therefore not fixed, but can be varied to take account of cations with multiple charges. For example, the formula [Cat][X⁻] should be understood to include ionic liquids having the formulae [Cat²][X⁻]$_2$; [Cat³⁺][X⁻]$_3$ and so on. In addition, [Cat⁺] may represent a single cationic species or a mixture of more than one cationic species.

Ionic liquids for use according to the present invention preferably have a melting point of 250° C. or less, more preferably 150° C. or less, still more preferably 100° C. or less, still more preferably 80° C. or less, and most preferably, the ionic liquid has a melting point below 30° C. However, any compound that meets the criteria of being a salt (consisting of a cation and an anion) and which is liquid at the operating temperature and pressure of the process may be defined as an ionic liquid for the purposes of the present invention.

As noted above, it is well known in the art that the properties of ionic liquids may be 'tuned' by altering the nature of the cations and the anions. In particular, in the methods of the invention, the structure of the cation or cations may be selected so as to obtain an ionic liquid having desired rheological and physical properties, such as liquid range, melting point, viscosity, hydrophobicity and lipophilicity. The selection of suitable cations to obtain ionic liquids having specific properties is well established in the art, and can readily be undertaken by a skilled person.

In one preferred embodiment of the invention, the ionic liquid is hydrophobic.

As used herein, the term "metal" should be understood to include both elemental metals and metal alloys having an oxidation state of zero, and metal compounds, such as metal oxides or metal sulfides, that have an oxidation state above zero. In addition, the metal may be combined with other substances, for instance, the metal may be in the form of a metal ore, the metal may be a comprised within a gaseous or liquid hydrocarbon substance, or the metal may be in an aqueous solution or suspension.

The term "metal" is also intended to encompass metalloids that behave in the same way as metals in the process of the invention. Thus, the term "metal" should be interpreted as including silicon, germanium, arsenic, selenium, antimony, tellurium, and polonium, and compounds thereof, as well as alkali metals, alkaline earth metals, transition metals, lanthanides, actinides, aluminium, indium, tin, thallium, lead, and bismuth, and compounds thereof.

Preferably, the metal comprises one or more of silicon, germanium, arsenic, selenium, antimony, tellurium, and polonium, transition metals, lanthanides, actinides, aluminium, indium, tin, thallium, lead, and bismuth.

In one embodiment, the method of the invention may be used for the dissolution of a precious metal selected from gold, silver, platinum, palladium, rhodium and iridium.

In another embodiment, the method of the invention may be used for the dissolution of a toxic heavy metal selected from cadmium, mercury, indium, thallium, germanium, tin, lead, arsenic, antimony, bismuth, selenium, tellurium and polonium. In particular, the method of the invention may be used for the dissolution of mercury.

In a further embodiment, the method of the invention may be used for the dissolution of a metal selected from silicon and germanium.

In a further embodiment, the method of the invention may be used for the dissolution of a metal selected from the lanthanides and actinides.

In yet a further embodiment, the method of the invention may be used for the dissolution of a radioactive metal selected from technetium, promethium, bismuth, polonium and the actinides.

In one embodiment of the invention, it is preferred that the metal is initially in an oxidation state below the maximum oxidation state of the metal (for example 0, +1 or +2) and is oxidised in contact with the ionic liquid to a higher oxidation state, with concomitant reduction of the perhalide anion to three halide anions. In a preferred embodiment, the metal is more soluble in the ionic liquid after oxidation to the higher oxidation state. In a further preferred embodiment, the metal in the higher oxidation state forms a complex ion with one or more halide anions that are formed in the reduction of the perhalide anion, and more preferably, the complex ion is a halometallate anion. As a representative example, elemental mercury(0) reacts with an ionic liquid such as 1-butyl-3-methylimidazolium tribromide to form a mercury(II) species which is complexed by bromide anions to form a bromomercurate(II) anion.

Without being bound by any particular theory, it is believed that ionic liquids comprising perhalide ions can oxidise metals and metal compounds, and that the halide ions formed in the oxidation step can coordinate to the oxidised metal to facilitate dissolution of the oxidative metal in the ionic liquid.

Dissolution of metals in the ionic liquids by a method of oxidising the metal from a low to a higher oxidation state relies on the ability of the perhalide anion present in the ionic liquid to oxidise the metal. It is well known that the oxidising power of halogens follows the order $Cl_2>ClBr>Br_2>I_2$, and the half-cell redox potentials of many metals are known from the electrochemical series (see for example *CRC Handbook of Chemistry and Physics, 87th Ed.*, CRC Press, 2006). The oxidising power of the ionic liquid solvent can be modified and controlled by the appropriate selection of the halogen constituents of the perhalide anion. As a general rule, metals can be dissolved if the metal substance is capable of oxidation by the respective anion present in the ionic liquid. The skilled person is readily capable of selecting ionic liquids with sufficient oxidation potential to oxidise a specific metal by the selection of a suitable perhalide component of the ionic liquid. The following series shows the increase in the oxidation potentials of perhalide anions from $[I_3]^-$ (lowest oxidation potential) to $[Cl_3]^-$ (highest oxidation potential):

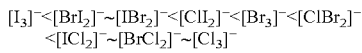

In accordance with the present invention, the metal is preferably contacted with the ionic liquid at a temperature of from −80° C. to 200° C., more preferably 0° C. to 150° C., and most preferably 20° C. to 100° C. The dissolution of metals is typically accelerated when the metal is contacted with the ionic liquid at elevated temperatures.

The metal is preferably contacted with the ionic liquid at atmospheric pressure (approximately 100 kPa), although pressures above or below atmospheric pressure may be used if desired. For instance, the process may be conducted at a pressure of from 10 kPa to 10000 kPa, more preferably from 20 kPa to 1000 kPa, still more preferably 50 to 200 kPa, and most preferably 80 to 120 kPa. As noted above, however, the ionic liquid must be liquid at the operating temperature and pressure of the process of the invention.

It will therefore be appreciated by the skilled person that the above operating temperature and pressure ranges may, in some cases, be further limited by the temperature and pressure ranges in which a selected ionic liquid is in liquid form.

The molar ratio of metal atoms in the metal to perhalide anions in the ionic liquid is preferably in the range of 1:0.5 to 1:10,000, more preferably 1:1 to 1:1000, still more preferably 1:1 to 1:100, and most preferably 1:1 to 1:10.

In one embodiment, dissolution of the metal in the ionic liquid is assisted by agitating the mixture of the ionic liquid and the metal, for example by stirring, shaking, vortexing or sonicating.

In another aspect, the present invention provides a method for reprocessing a spent nuclear fuel comprising a radioactive metal, which comprises dissolving the radioactive metal in an ionic liquid as defined above. The spent nuclear fuel may comprise an actinide oxide, and most preferably the actinide oxide comprises a uranium oxide and/or a plutonium oxide.

In a further preferred embodiment, the spent nuclear fuel comprises cladding materials comprising metals which are dissolved together with the radioactive metal. Nuclear fuel cladding materials which may be dissolved according to this aspect of the invention include zirconium alloys.

In a further aspect, the present invention provides a method for removing metals from metal-containing materials comprising contacting the metal-containing material with an ionic liquid as defined above. In accordance with this aspect of the invention, the metal-containing material may be a gaseous, liquid or solid material, and may comprise any metal as defined above.

In one embodiment, the metal-containing material is a metal-containing hydrocarbon gas, such as a natural gas and/or a refinery gas. For instance, toxic and heavy metals, such as mercury may be removed from hydrocarbon gases in accordance with this aspect of the invention.

In a further embodiment, the metal-containing material is a metal-containing liquid hydrocarbon. Examples of metal-containing liquid hydrocarbons which may be treated according to this aspect of the invention include liquefied natural gas; light distillates, e.g. comprising liquid petroleum gas, gasoline, and/or naphtha; natural gas condensates; middle distillates, e.g. comprising kerosene and/or diesel; heavy distillates, e.g. fuel oil; and crude oils.

In another embodiment, the metal-containing substance is a metal-containing aqueous liquid. This aspect of the invention may be applied to the remediation of metal-contaminated groundwater; the recovery of metals from aqueous metal leachates comprising metals leached from mineral ores using aqueous leaching agents; the recovery of valuable catalyst metals, such as transition metal catalysts, from aqueous solutions of the catalyst metals; and to the remediation of aqueous by-products of nuclear fuel processing or reprocessing.

In yet another embodiment, the metal-containing material is a metal-containing solid. Metal-containing mineral ores may be treated with an ionic liquid as described above to leach metals, for example precious metals, from the ore. This aspect of the invention may also be used to recover precious and/or heavy metals from waste electronic apparatus, such as circuit boards and electronic components, and other waste consumer goods. This aspect of the invention may further be used to recover catalyst metals, for example transition metal catalysts such as platinum, palladium, rhodium, iridium, ruthenium, osmium, from solid supports.

In a further aspect, the present invention provides a method for etching the surface of a metalloid, comprising contacting an exposed surface of the metalloid with an ionic liquid as described above. Etching of metalloids according to the method of the invention may be used in the manufacture of microelectromechanical systems (MEMS) and metalloid semiconductors. Preferably, in this aspect of the invention, the metalloid semiconductor comprises silicon and/or gallium.

In still a further aspect, the present invention provides novel metal-ionic liquid compositions obtainable by a method comprising contacting the metal with an ionic liquid having the formula:

wherein [Cat$^+$] represents one or more cationic species as defined above, and

[X$^-$] represents one or more perhalide anions as defined above, wherein the ionic liquid is free of additional solvents and/or oxidants.

In yet a further aspect there is provided an ionic liquid comprising a complex halometallate anion obtainable from an ionic liquid comprising a perhalide anion as described above.

The metal-ionic liquid compositions may comprise a molar ratio of dissolved metal to the ionic liquid of at least 0.05:1.

The metal-ionic liquid compositions may comprise a molar ratio of dissolved metal to the ionic liquid of at least 0.1:1.

The metal-ionic liquid compositions may comprise a molar ratio of dissolved metal to the ionic liquid of at least 0.2:1.

The metal-ionic liquid compositions may comprise a molar ratio of dissolved metal to the ionic liquid of at least 0.4:1.

The metal-ionic liquid compositions may comprise a molar ratio of dissolved metal to the ionic liquid of at least 0.6:1.

The metal-ionic liquid compositions may comprise a molar ratio of dissolved metal to the ionic liquid of at least 0.8:1.

The metal-ionic liquid compositions may comprise a molar ratio of dissolved metal to the ionic liquid of at least 0.9:1.

The metal-ionic liquid compositions may comprise a molar ratio of dissolved metal to the ionic liquid of at least 1:1.

The aspects of the present inventions will now be described by way of example.

EXAMPLES

Example 1: Synthesis of Perhalide Ionic Liquids

Ionic liquids with mixed perhalide anions ($[XY_2]^-$, where X=Cl or Br, and Y=Br or I) were prepared with dialkylimidazolium, tetraalkylammonium, tetraalkylphosphonium and alkylmethylpyridinium cations (see Table 1) following literature procedures. Briefly, liquid bromine or solid iodine was added to an appropriate amount of organic halide salt to achieve the desired 1:1 molar stoichiometry, generating perhalide anions. The mixtures were mixed overnight at room temperature to yield the respective perhalide ionic liquids, which were characterised by mass spectrometry and thermogravimetric analysis (TGA).

Mass spectrometry identified the presence of mass ions for the cation ($[Q]^+$) and perhalide anions ($[XY_2]^-$) in each case. TGA demonstrates that the volatility of the halogen has been significantly reduced by incorporation into the ionic liquid. Mass losses, over the temperature range 150 to 300° C., corresponded to initial loss of the most volatile dihalogen from the ionic liquid ($Br_2$ or ClBr) and associated thermal decomposition of the organic halide salt consistent with literature decomposition temperatures.

TABLE 1

Ionic liquids prepared and physical state

| Cation[a] | Anion | Physical state at room temperature | Thermal Stability (determined by TGA) |
|---|---|---|---|
| $[C_4mim]^+$ | $[BrI_2]^-$ | liquid | 208° C. |
| $[C_4mim]^+$ | $[Br_3]^-$ | liquid | 185° C. |
| $[C_4mim]^+$ | $[ClI_2]^-$ | liquid | 205° C. |
| $[C_4mim]^+$ | $[ClBr_2]^-$ | liquid | 152° C. |
| $[P_{6,6,6,14}]^+$ | $[ClBr_2]^-$ | liquid | 194° C. |
| $[C_2C_2im]^+$ | $[Br_3]^-$ | liquid | 156° C. |
| $[N_{4,4,4,1}]^+$ | $[Br_3]^-$ | crystalline | 176° C. |
| $[C_4^4pic]^+$ | $[Br_3]^-$ | crystalline | 155° C. |

[a]$[C_4mim]^+$ = 1-butyl-3-methylimidazolium; $[P_{6,6,6,14}]^+$ = trihexyltetradecylphosphonium; $[C_2C_2im]^+$ = 1,3-diethylimidazolium; $[N_{4,4,4,1}]^+$ = tributylmethylammonium; $[C_4^4pic]^+$ = 1-butyl-4-methylpyridinium (4-picolinium).

Comparative Example 2: The Solubility of Bromine in Non-Halide Ionic Liquids

Bromine was not found to be completely miscible at 1:1 molar ratios with either 1-butylpyridinium bistriflimide or with 1-butyl-3-methylimidazolium hydrogensulfate, and extensive evolution of bromine vapour was observed from the ionic liquid/bromine mixtures on standing under ambient conditions.

Example 3: Dissolution of Metals

A range of powdered elemental metal samples (approximately 0.1 g each, accurately measured) were mixed with 1-butyl-3-methylimidazolium tribromide (1.0 mL) producing mixtures of approximately 5 wt % metal in ionic liquid. The mixtures were stirred with heating to 60° C. for 72 h, then cooled to room temperature and filtered through 2 micron nylon filters. For each sample, approximately 0.1 g of the filtrate was accurately weighed, and digested in 50 mL of 5% w/w nitric acid and the metal content determined by inductively coupled plasma (ICP) analysis. The percentage of the metal sample dissolved in the ionic liquid in each test is shown in Table 2.

TABLE 2

Metal dissolution test results.

| Metal | Percentage of metal dissolved in ionic liquid |
|---|---|
| Aluminium | 5 |
| Chromium | 49 |
| Copper | 94 |
| Iron | 71 |
| Antimony | 98 |
| Titanium | trace |
| Tungsten | 7 |

Example 4: Qualitative Screening of Mercury Solubilisation

Qualitative screening of elemental mercury solubility in the ionic liquid systems has been made by visually observing the state of a single droplet of mercury (ca. 0.05 g) stirred in ca. 1-2 mL of ionic liquid at room temperature and at 60° C. Complete dissolution under these conditions would give mercury loadings concentrations in the order of 25-50,000 ppm (about 5 mol %).

TABLE 3

Perhalide ionic liquids screened and observations on mercury solubility.

| Cation[a] | Anion | Mercury Solubility[b] |
|---|---|---|
| $[C_4mim]^+$ | $[BrI_2]^-$ | no solubility observed visually |
| $[C_4mim]^+$ | $[Br_3]^-$ | soluble |
| $[C_4mim]^+$ | $[ClI_2]^-$ | no solubility observed visually |
| $[C_4mim]^+$ | $[ClBr_2]^-$ | soluble |
| $[P_{6,6,6,14}]^+$ | $[ClBr_2]^-$ | soluble |
| $[C_2C_2im]^+$ | $[Br_3]^-$ | soluble |
| $[N_{4,4,4,1}]^+$ | $[Br_3]^-$ | soluble |
| $[C_4^4pic]^+$ | $[Br_3]^-$ | solvent solid under test conditions |

[a]$[C_4mim]^+$ = 1-butyl-3-methylimidazolium; $[P_{6,6,6,14}]^+$ = trihexyltetradecylphosphonium; $[C_2C_2im]^+$ = 1,3-diethylimidazolium; $[N_{4,4,4,1}]^+$ = tributylmethylammonium; $[C_4^4pic]^+$ = 1-butyl-4-methylpyridinium (4-picolinium).
[b]Approximately 0.05 g mercury was contacted with 1-2 mL of ionic liquid, mercury solubility at least 25,000 ppm.

Example 5: Dissolution of Bulk Mercury

Elemental mercury (1.213 g, 6.05 mmol) was added to 1-butyl-3-methylimidazolium tribromide (4.52 g, 12.1 mmol) and heated at 70° C. with stirring in a sealed vessel. The dense metallic mercury drop was observed to decrease in volume over time, and after 2 hours the mercury completely dissolved into the red ionic liquid solution. On cooling to room temperature, no precipitation of mercury or mercury-containing species was observed.

Example 6: Preparation of 1-butyl-3-methylimidazolium tribromomercurate(II)

Elemental mercury (3.129 g, 15.6 mmol) was added to 1-butyl-3-methylimidazolium tribromide (5.91 g, 15.6 mmol) and heated at 70° C. with stirring in a sealed vessel. The dense metallic mercury drop was observed to decrease in volume over time, and after 4 hours the mercury completely dissolved with a change in the colour of the ionic liquid from deep red to pale yellow on complete dissolution of mercury and conversion of tribromide anions to tribromomercurate(II) anions. On cooling, the new ionic liquid, 1-butyl-3-methylimidazolium tribromomercurate(II) crystallised as a pale yellow solid at 40° C.

Example 7: Preparation of bis(1,3-diethylimidazolium)tetrabromomercurate(II)

Elemental mercury was added to 1,3-diethylimidazolium tribromide and heated at 70° C. with stirring in a sealed vessel. The dense metallic mercury drop was observed to decrease in volume and after 4 hours the mercury completely dissolved in the red ionic liquid. Cooling to room temperature and standing resulted in the formation of crystals from the ionic liquid which were isolated and determined to be bis(1,3-diethylimidazolium)tetrabromomercurate(II) by single crystal X-ray diffraction.

Example 8: Dissolution of Mercury in Iodine-Based Perhalide Ionic Liquids

Bulk dissolution of elemental mercury was not observed in iodine-based perhalide ionic liquids, [C$_4$mim][ClI$_2$] and [C$_4$mim][BrI$_2$] or with 1-butylpyridinium bistriflimide or with 1-butyl-3-methylimidazolium hydrogen sulfate under the conditions described in Example 4.

The invention claimed is:

1. A method of extracting metals and metal compounds from aqueous solutions comprising contacting the aqueous solution with an ionic liquid having the formula:

[Cat$^+$][X$^-$]

wherein: [Cat$^+$] represents one or more cationic species, and
[X$^-$] represents one or more perhalide anions, wherein the ionic liquid is free of additional solvents and/or oxidants.

2. A method according to claim 1, wherein [X$^-$] comprises at least one perhalide anion selected from [I$_3$]$^-$, [BrI$_2$]$^-$, [Br$_2$I]$^-$, [ClI$_2$]$^-$, [Br$_3$]$^-$, [ClBr$_2$], [BrCl$_2$]$^-$, [ICl$_2$]$^-$, or [Cl$_3$]$^-$.

3. A method according to claim 2, wherein [X$^-$] comprises at least one perhalide anion selected from [BrI$_2$]$^-$, [Br$_2$I]$^-$, [ClI$_2$]$^-$, [ClBr$_2$]$^-$, [BrCl$_2$]$^-$; or [ICl$_2$]$^-$.

4. A method according to claim 2, wherein [X$^-$] comprises at least one perhalide anion selected from [I$_3$]$^-$, [Br$_3$]$^-$, or [Cl$_3$]$^-$.

5. A method according to claim 1, wherein [Cat$^+$] is a cationic species selected from the group consisting of: ammonium, azaannulenium, azathiazolium, benzimidazolium, benzofuranium, benzotriazolium, borolium, cinnolinium, diazabicyclodecenium, diazabicyclononenium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxathiazolium, pentazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, selenozolium, sulfonium, tetrazolium, iso-thiadiazolium, thiazinium, thiazolium, thiophenium, thiuronium, triazadecenium, triazinium, triazolium, iso-triazolium, and uronium.

6. A method according to claim 5 wherein [Cat$^+$] is a cationic species selected from the group consisting of:

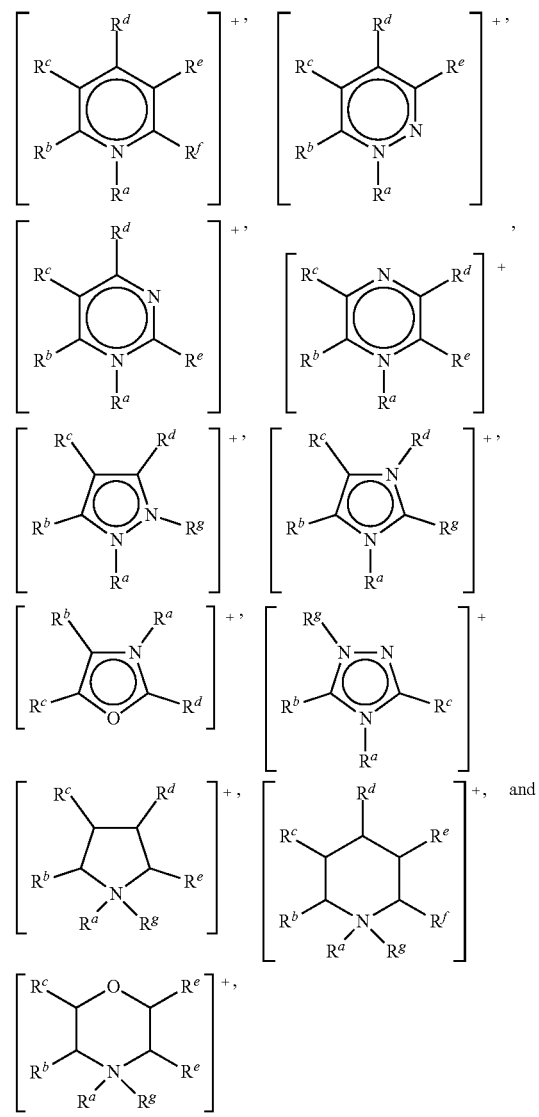

wherein: R$^a$, R$^b$, R$^c$, R$^d$, R$^e$, R$^f$ and R$^g$ are each independently selected from hydrogen, a C$_1$ to C$_{30}$, straight chain or branched alkyl group, a C$_3$ to C$_8$ cycloalkyl group, or a C$_6$ to C$_{10}$ aryl group, or any two of R$^b$, R$^c$, R$^d$, R$^e$ and R$^f$ attached to adjacent carbon atoms form a methylene chain —(CH$_2$)$_q$— wherein q is from 3 to 6; and wherein said alkyl, cycloalkyl or aryl groups or said methylene chain are unsubstituted or may be substituted by one to three groups selected from: C$_1$ to C$_6$ alkoxy, C$_2$ to C$_{12}$ alkoxyalkoxy, C$_3$ to C$_8$ cycloalkyl, C$_6$ to C$_{10}$ aryl, C$_7$ to C$_{10}$ alkaryl, C$_7$ to C$_{10}$ aralkyl, —CN, —OH, —SH, —NO$_2$, —CO$_2$R$^x$, —OC(O)R$^x$, —C(O)R$^x$, —C(S)R$^x$, —CS$_2$R$^x$, —SC(S)R$^x$, —S(O) (C$_1$ to C$_6$)alkyl, —S(O)O(C$_1$ to C$_6$)alkyl, —OS(O)(C$_1$ to C$_6$)alkyl, —S(C$_1$ to C$_6$)alkyl, —S—S(C$_1$ to C$_6$ alkyl), —NR$^x$C(O)NR$^y$R$^z$, —NR$^x$C(O)OR$^y$, —OC(O) NR$^y$R$^z$, —NR$^x$C(S)OR$^y$, —OC(S)NR$^y$R$^z$, —NR$^x$C(S) SR$^y$, —SC(S)NR$^y$R$^z$, —NR C(S)NR$^y$R$^z$, —C(O) NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl.

7. A method according to according to claim 6 wherein [Cat$^+$] is a cationic species selected from the group consisting of:

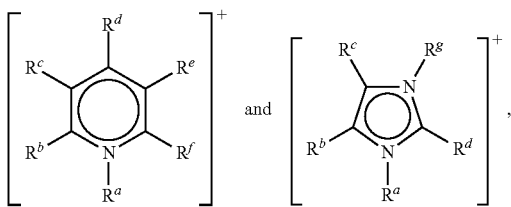

wherein: $R^a$, $R^b$, $R^c$, $R^d$, $R^e$, $R^f$ and $R^g$ are as defined in claim 6.

8. A method according to according to claim 7 wherein [Cat$^+$] is a cationic species selected from the group consisting of:

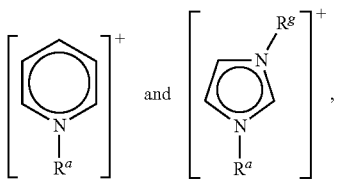

wherein: $R^a$ and $R^g$ are as defined in claim 6.

9. A method according to claim 5, wherein [Cat$^+$] is selected from the group consisting of:

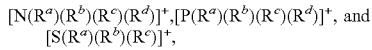

wherein: $R^a$, $R^b$, $R^c$, and $R^d$ are each independently selected from a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —(CH$_2$)$_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO$_2$, —CO$_{-2}$R$^x$, —OC(O)R$^x$, —C(O)R$^x$, —C(S)R$^x$, —CS$_2$R$^x$, —SC(S)R$^x$, —S(O)O(C$_1$ to C$_6$)alkyl, —OS(O)(C$_1$ to C$_6$)alkyl, —S(C$_1$ to C$_6$)alkyl, —S—S(C$_1$ to C$_6$)alkyl, —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^1$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl, and wherein one of $R^a$, $R^b$, $R^c$, and $R^d$ may also be hydrogen.

10. A method according to claim 1, wherein the ionic liquid is hydrophobic.

11. A method according to claim 1, wherein the metal is oxidized from an initial oxidation state below its maximum oxidation state to a higher oxidation state by reaction with the ionic liquid.

12. A method according to claim 11, wherein the metal is more soluble in the ionic liquid when in the higher oxidation state than when in the initial oxidation state.

13. A method according to claim 11, wherein the oxidized metal forms a complex ion with one or more halide anions formed during the oxidation.

14. A method according to claim 13, wherein the complex ion is a halometallate anion.

15. A method according to claim 1, wherein the metal comprises a metal selected from transition metals, lanthanides, actinides, aluminium, silicon, germanium, arsenic, selenium, indium, tin, antimony, tellurium, thallium, lead, bismuth or polonium.

16. A method according to claim 15, wherein the metal comprises a precious metal selected from gold, silver, platinum, palladium, rhodium and iridium.

17. A method according to claim 15, wherein the metal comprises a toxic heavy metal selected from cadmium, mercury, indium, thallium, germanium, tin, lead, arsenic, antimony, bismuth, selenium, tellurium and polonium.

18. A method according to claim 17, wherein the metal comprises mercury.

19. A method according to claim 17, wherein the metal comprises a metal selected from silicon and germanium.

20. A method according to claim 15, wherein the metal comprises a lanthanide or an actinide.

21. A method according to claim 1, wherein the metal comprises a metal in elemental form.

22. A method according to claim 1, wherein the metal comprises a metal oxide or a metal sulfide.

23. A method according to claim 1, wherein the metal is added to the ionic liquid at a temperature of from −80° C. to 200° C.

24. A method according to claim 1, wherein the metal is added to the ionic liquid at atmospheric pressure.

* * * * *

UNITED STATES PATENT AND TRADEMARK OFFICE
CERTIFICATE OF CORRECTION

PATENT NO. : 11,198,921 B2  
APPLICATION NO. : 16/372614  
DATED : December 14, 2021  
INVENTOR(S) : Rogers et al.

Page 1 of 1

It is certified that error appears in the above-identified patent and that said Letters Patent is hereby corrected as shown below:

On the Title Page

Item (30):  
"Foreign Application Priority Data: Apr. 6, 2009 (GB).................0905894"  
Should read:  
--Foreign Application Priority Data: Apr. 6, 2009 (GB).................0905894.2--

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*